(12) United States Patent
Pandey

(10) Patent No.: US 9,814,369 B2
(45) Date of Patent: Nov. 14, 2017

(54) PIVOTING THREE-DIMENSIONAL VIDEO ENDOSCOPE

(75) Inventor: Ashwini K. Pandey, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 1060 days.

(21) Appl. No.: 13/437,222

(22) Filed: Apr. 2, 2012

(65) Prior Publication Data

US 2012/0289781 A1    Nov. 15, 2012

Related U.S. Application Data

(60) Provisional application No. 61/485,663, filed on May 13, 2011.

(51) Int. Cl.
| | | |
|---|---|---|
| *A61B 1/04* | (2006.01) | |
| *A61B 1/00* | (2006.01) | |
| *A61B 1/313* | (2006.01) | |
| *A61B 90/00* | (2016.01) | |
| *A61B 17/34* | (2006.01) | |
| *A61B 17/00* | (2006.01) | |
| *A61B 90/50* | (2016.01) | |

(52) U.S. Cl.
CPC ...... *A61B 1/00177* (2013.01); *A61B 1/00193* (2013.01); *A61B 1/313* (2013.01); *A61B 90/361* (2016.02); *A61B 1/00045* (2013.01); *A61B 17/3417* (2013.01); *A61B 90/50* (2016.02); *A61B 2017/00734* (2013.01); *A61B 2090/502* (2016.02)

(58) Field of Classification Search
CPC ............ A61B 1/00087; A61B 1/00101; A61B 1/00147; A61B 1/00177; A61B 1/00193
USPC .......................................................... 600/102
See application file for complete search history.

(56) References Cited

U.S. PATENT DOCUMENTS 3,520,587 A  *  7/1970  Ouchi et al. .................. 359/376
3,534,729 A     10/1970  Sakamoto
(Continued)

FOREIGN PATENT DOCUMENTS

| CN | 202018517    | 10/2011 |
|----|--------------|---------|
| KR | 100947624 B1 | 3/2010  |
| WO | WO 99/58044 A1 | 11/1999 |

OTHER PUBLICATIONS

European Search Report for EP12167685—dated Aug. 8, 2012.

*Primary Examiner* — Anhtuan T Nguyen
*Assistant Examiner* — Jae Woo

(57) ABSTRACT

A surgical camera assembly includes a proximal member defining a longitudinal axis and a distal member defining a pointed tip configured to puncture tissue to permit insertion of the surgical camera assembly therethrough. The distal member is pivotably coupled to the proximal member and is movable relative thereto between a first position, wherein the distal member is aligned with the longitudinal axis, and a second position, wherein the distal member is angled off the longitudinal axis. First and second surgical cameras are disposed within the distal member in fixed position and longitudinally-spaced relative to one another. Each of the cameras is oriented to define a viewing area in a direction extending from an outer lateral periphery of the distal member. The cameras are configured to produce video images that are used in conjunction with one another to provide a three-dimensional video image of the internal surgical site.

6 Claims, 3 Drawing Sheets

(56) References Cited

U.S. PATENT DOCUMENTS

| | | | |
|---|---|---|---|
| 3,556,085 A * | 1/1971 | Takahashi | 600/129 |
| 4,310,849 A | 1/1982 | Glass | |
| 4,489,728 A | 12/1984 | Matsuo et al. | |
| 4,589,723 A | 5/1986 | Doi et al. | |
| 4,709,263 A | 11/1987 | Brumage | |
| 4,784,463 A * | 11/1988 | Miyazaki | 385/117 |
| 4,854,301 A * | 8/1989 | Nakajima | 600/102 |
| 4,862,873 A | 9/1989 | Yajima et al. | |
| 4,867,404 A * | 9/1989 | Harrington et al. | 606/46 |
| 5,334,150 A * | 8/1994 | Kaali | 604/164.08 |
| 5,368,015 A * | 11/1994 | Wilk | 600/104 |
| 5,379,754 A | 1/1995 | Tovey et al. | |
| 5,385,138 A * | 1/1995 | Berry | 600/166 |
| 5,613,936 A * | 3/1997 | Czarnek et al. | 600/166 |
| 5,846,185 A * | 12/1998 | Carollo et al. | 600/166 |
| 5,966,168 A * | 10/1999 | Miyazaki | 348/68 |
| 6,144,762 A | 11/2000 | Brooks | |
| 6,450,950 B2 * | 9/2002 | Irion | 600/170 |
| 2002/0007110 A1 | 1/2002 | Irion | |
| 2007/0265502 A1 * | 11/2007 | Minosawa et al. | 600/173 |
| 2008/0027279 A1 | 1/2008 | Abou El Kheir | |
| 2010/0198009 A1 | 8/2010 | Farr et al. | |

* cited by examiner

PIVOTING THREE-DIMENSIONAL VIDEO ENDOSCOPE

CROSS REFERENCE TO RELATED APPLICATION

The present application claims the benefit of and priority to U.S. Provisional Application Ser. No. 61/485,663, filed on May 13, 2011, the entire contents of which are incorporated herein by reference.

BACKGROUND

Technical Field

The present disclosure relates to surgical instruments, and more particularly, to a pivotable surgical camera assembly for three-dimensional viewing of an internal surgical site.

Background of Related Art

Endoscopic surgical procedures are minimally invasive procedures in which operations are carried out within the body by using elongated instruments inserted through small entrance openings in the body. Minimally invasive procedures are desirable in that they allow for quicker recovery time and shorter hospital stays as compared to open surgical procedures. Minimally invasive procedures also leave minimal scarring (both internally and externally) and reduce patient discomfort during the recovery period. However, because the interior dimensions of the entrance openings into the body are necessarily small, only elongated, small diametered instrumentation may be used to access the internal surgical site.

During a typical minimally-invasive surgical procedure, a surgical camera, or endoscope, is inserted through an access opening in the body to permit the surgeon to view the internal site. Where three-dimensional viewing of the internal surgical site is desired, multiple cameras, or an endoscope including multiple cameras disposed thereon, are inserted into the surgical site through additional access openings formed within the body. However, movement of these three-dimensional cameras during the surgical procedure may cause distortion of the video image. Further, the patient may experience discomfort during manipulation of the cameras within the surgical site and/or during insertion of the cameras into the internal surgical site.

SUMMARY

In accordance with one embodiment of the present disclosure, a surgical camera assembly is provided. The surgical camera assembly includes an elongated proximal member defining a longitudinal axis and an elongated distal member defining a pointed distal tip configured to puncture tissue to permit insertion of the surgical camera assembly at least partially into an internal surgical site. The distal member is pivotably coupled to the proximal member and is movable relative thereto between a first position, wherein the distal member is substantially aligned with the proximal member and the longitudinal axis, and a second position, wherein the distal member is angled off of the longitudinal axis. First and second surgical cameras are fixedly disposed within the elongated distal member. Each of the first and second surgical cameras is oriented to define a viewing area in a direction extending from an outer lateral periphery of the distal member. The first and second surgical cameras are fixed in position relative to one another and are longitudinally spaced-apart from one another. The first and second surgical cameras are configured to produce first and second video images, respectively, that are used in conjunction with one another to provide a three-dimensional video image of the internal surgical site.

In one embodiment, an illumination source disposed within the distal member between the first and second surgical cameras is provided. The illumination source is configured to illuminate the internal surgical site to facilitate imaging thereof.

In another embodiment, a support platform including a base and a support arm is provided. The support arm is configured to releasably support the surgical camera assembly at a free end thereof. Further, the support arm may be operable to manipulate the surgical camera assembly for insertion of the surgical camera into and positioning of the surgical camera within the internal surgical site. The support arm may be manually or robotically controlled.

A method of visualizing an internal surgical site is also provided in accordance with the present disclosure. The method includes providing a surgical camera assembly according to any of the embodiments above. The method further includes advancing the surgical camera assembly relative to tissue to puncture tissue with the pointed distal tip of the distal member and advancing the surgical camera assembly further through the puncture in tissue to position the surgical camera assembly at least partially within the internal surgical site. The distal member is then pivoted relative to the proximal member from a first position, wherein the distal member is substantially aligned with the proximal member and the longitudinal axis, to a second position, wherein the distal member is angled off of the longitudinal axis, to orient the surgical cameras in a desired viewing direction within the internal surgical site. The method further includes viewing a three-dimensional video image of the internal surgical site as viewed in the viewing direction. The three-dimensional video image is produced by synthesizing the first and second video images of first and second surgical cameras, respectively.

In one embodiment, the surgical camera assembly is rotated about the longitudinal axis thereof to orient the surgical cameras in a desired viewing direction within the internal surgical site.

In another embodiment, the method includes coupling the surgical camera assembly to a support platform. The support platform may be operable to manipulate the surgical camera assembly to advance the surgical camera assembly to puncture tissue, to advance the surgical camera further into (or retracted the surgical camera from) the surgical site, and/or to pivot the distal member relative to the longitudinal axis.

BRIEF DESCRIPTION OF THE DRAWINGS

Various embodiments of the subject instrument are described herein with reference to the drawings wherein.

DETAILED DESCRIPTION

Figure 1:
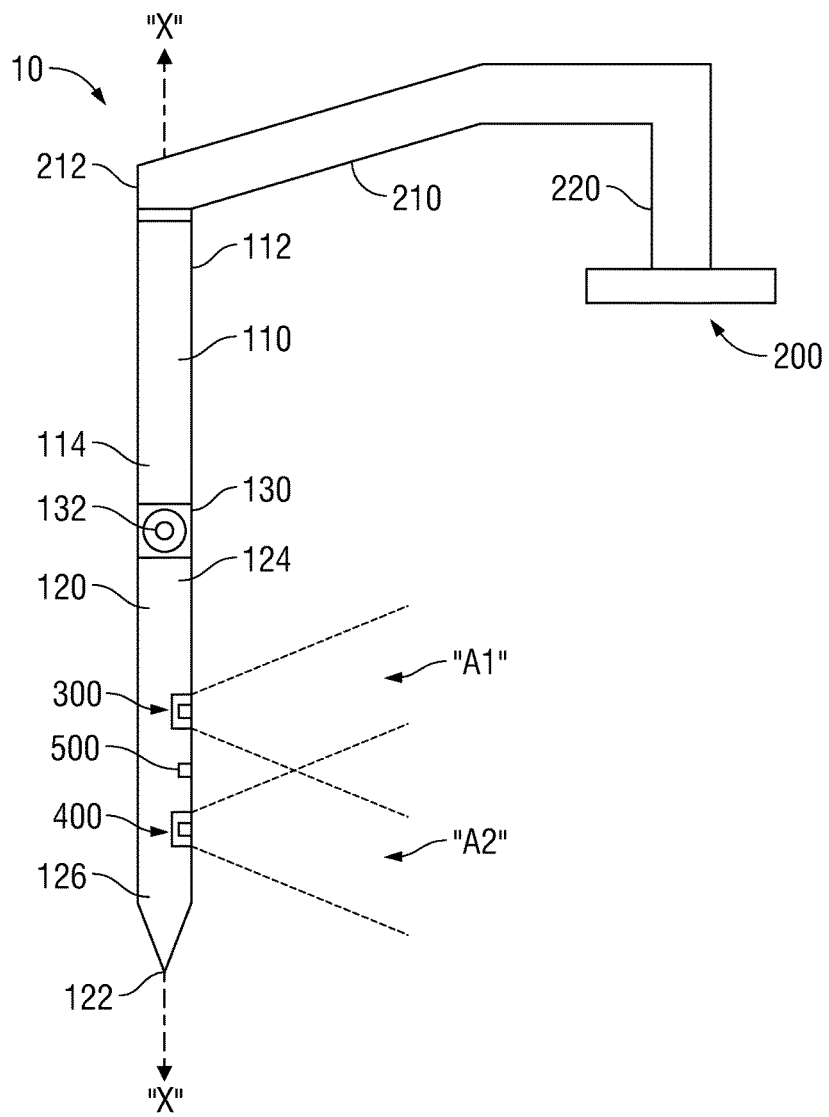
FIG. 1 is a side view a surgical camera assembly including a mounting platform provided in accordance with the present disclosure.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Figure 2:
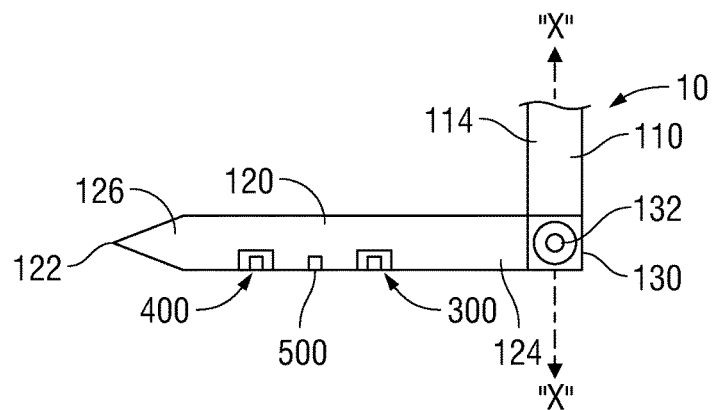
FIG. 2 is a side view of a distal portion of the surgical camera assembly of FIG. 1, wherein the distal portion of the surgical camera assembly is angled off of a longitudinal axis of the surgical camera assembly.

Referring now to FIGS. 1-2, a surgical camera assembly provided in accordance with the present disclosure is shown generally identified by reference numeral 10. Surgical camera assembly 10 defines a longitudinal axis "X-X" and generally includes a rigid, or semi-rigid elongated tubular proximal member 110, a rigid, or semi-rigid elongated tubular distal member 120 including a needle-shaped, or conically-shaped distal tip 122, and a pivot assembly 130 interconnecting proximal member 110 and distal member 120 to permit relative pivoting of distal member 120 relative to proximal member 110 and longitudinal axis "X-X." Proximal member 110 includes a proximal end 112 that is configured to releasably engage an arm 210 of support platform 200, e.g., via latching, threaded coupling, friction-fitting, etc, and a distal end 114 that is fixedly engaged to pivot assembly 130. Distal member 120 includes a proximal end 124 that is pivotably coupled to pivot assembly 130 and, thus, proximal member 110 via pivot pin 132 and a pointed distal tip 122 defined at distal end 126 thereof. Distal member 120 also includes surgical cameras 300, 400 disposed therein that, together, cooperate to produce a three-dimensional video image of the internal surgical site "S" (FIGS. 4-6), as will be described in greater detail below. Distal member 120 may further include an illumination source 500 disposed between surgical cameras 300, 400 (or otherwise positioned) to illuminate the surgical site "S" (FIGS. 4-6) for better visualization thereof.

Figure 4:
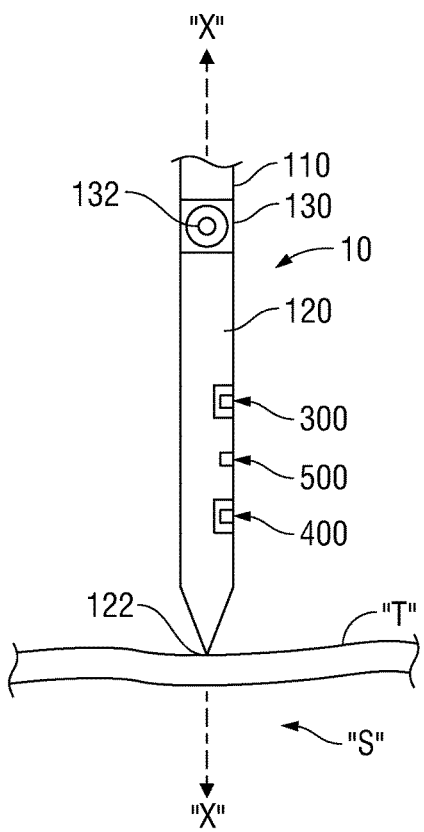
FIG. 4 is a side view of the surgical camera assembly of FIG. 1 shown puncturing tissue for insertion therethrough.
Figure 5:
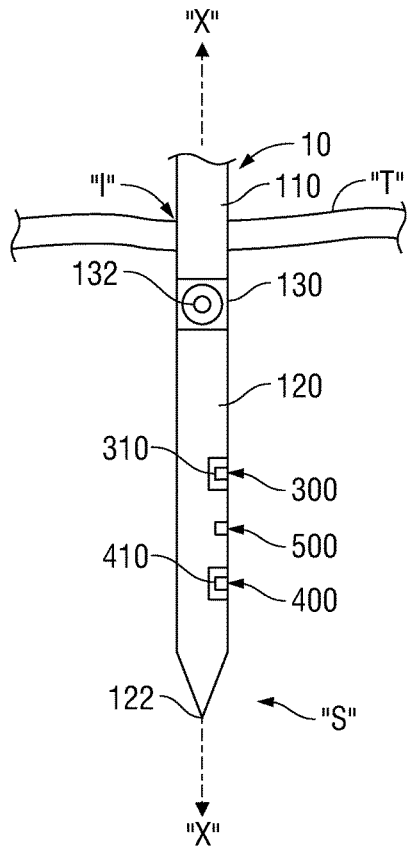
FIG. 5 is a side view of the surgical camera assembly of FIG. 1 shown disposed through tissue and within an internal surgical site.
Figure 6:
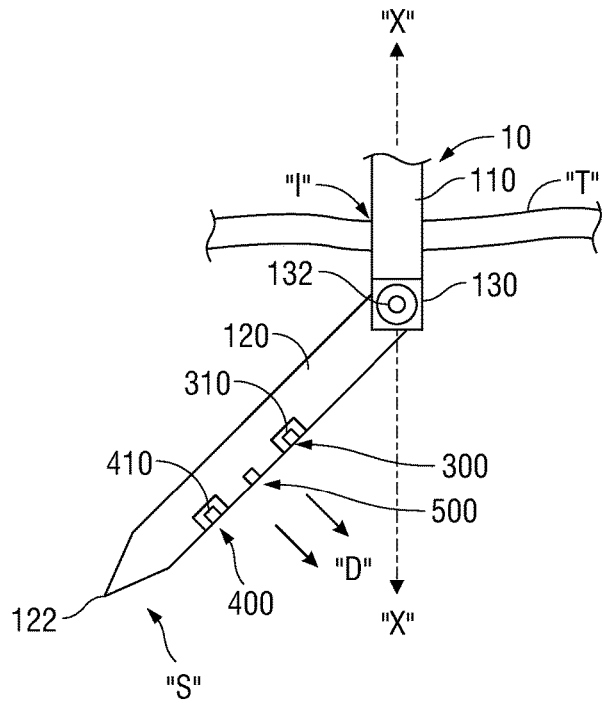
FIG. 6 is a side view of the surgical camera assembly of FIG. 1 shown disposed through tissue and within an internal surgical site, wherein the distal portion of the surgical camera assembly is angled off of the longitudinal axis of the surgical camera assembly.

As can be appreciated, and as will be described in greater detail below, pointed distal tip 122 of surgical camera assembly 10 facilitates insertion of surgical camera assembly 10 through tissue "T" (FIGS. 4-6), i.e., to puncture tissue "T" with distal tip 122 of surgical camera assembly 10, and into an internal surgical site "S" (FIG. 4-6) while minimizing trauma to tissue "T" (FIGS. 4-6). Further, providing an insertable distal tip 122 on surgical camera assembly 10 obviates the need for additional access instrumentation, e.g., trocars and/or cannulas, for creating an opening, inserting surgical camera assembly 10 within the opening and/or positioning surgical camera assembly 10 within the internal surgical site "S" (FIGS. 4-6).

As best shown in FIG. 2, and as mentioned above, distal member 120 is pivotably coupled to pivot assembly 130 and, thus, to proximal member 110 via pivot pin 132. More specifically, distal member 120 is pivotable about pivot pin 132 of pivot assembly 130 between an initial position, wherein distal member 120 is substantially aligned with proximal member 110 and longitudinal axis "X-X" of surgical camera assembly 10, and a second position, wherein distal member 120 is pivoted off of longitudinal axis "X-X." Distal member 120 may be configured to pivot relative to longitudinal axis "X-X" to a substantially perpendicular position (as shown in FIG. 2), or any suitable position therebetween. Further, distal member 120 may be configured for either uni-directional pivoting, i.e., where distal member 120 is pivotable off of longitudinal axis "X-X" in only a single direction, or bi-directional pivoting, i.e., where distal member 120 is pivotable off of longitudinal axis "X-X" in either direction. Bi-directional pivoting is advantageous in that, in conjunction with rotation of surgical camera assembly 10 about longitudinal axis "X-X," surgical cameras 300, 400 may be positioned for viewing any portion of an internal surgical site "S" (FIGS. 4-6). The pivoting of distal member 120 about pivot pin 132 of pivot assembly 130 may be mechanically-controlled, i.e., manually controlled, electrically-controlled, or electro-mechanically controlled.

Referring now to FIG. 1, support platform 200 includes a support arm 210 and a base 220. Base 220 is rigidly secured to a floor, or other stationary surface (not shown) to stabilize arm 210. Arm 210 extends from base 220 and may define any suitable configuration for inserting, manipulating and/or retaining surgical camera assembly 10 in position within the internal surgical site "S" (FIGS. 4-6). More particularly, arm 210 is configured to releasably engage proximal member 110 of surgical camera assembly 10 at free end 212 thereof and is operable to manipulate, translate, and/or rotate surgical camera assembly 10 relative to base 220. Arm 210 may be manually controlled, or robotically controlled to effect movement and/or manipulation of surgical camera assembly 10. Arm 210 of support platform 200 may further be configured to electrically couple to surgical camera assembly 10 for controlling the operation of surgical camera 10, i.e., to pivot distal member 120 relative to proximal member 110 and/or to operate surgical cameras 300, 400, as will be described in greater detail below. Alternatively, surgical camera assembly 10 may be independently operated separately from the operation of arm 210 of support platform 200.

Referring again to FIGS. 1-2, surgical camera assembly 10 includes first and second cameras 300, 400, respectively, disposed longitudinally along distal member 120 thereof. First and second cameras 300, 400, respectively, are spaced-apart from one another a suitable distance for providing three-dimensional imaging of the internal surgical site "S" (FIGS. 4-6) and are positioned substantially perpendicularly relative to longitudinal axis "X-X" when distal member 120 is disposed in the initial position, as shown in FIG. 1. More specifically, first and second cameras 300, 400, respectively, are each oriented to receive an image of the generally conically-shaped area "A1" and "A2," respectively, extending outwardly from the outer lateral periphery of distal member 120. As can be appreciated, the areas "A1" and "A2" substantially overlap one another, although, due to the offset of first and second cameras 300, 400, respectively, longitudinally along distal member 120, the images of areas "A1" and "A2" are offset relative to one another. As will be described below, this offset allows the images produced by surgical cameras 300, 400 to be synthesized to produce a three-dimensional image of the internal surgical site "S" (FIGS. 4-6).

Figure 3:
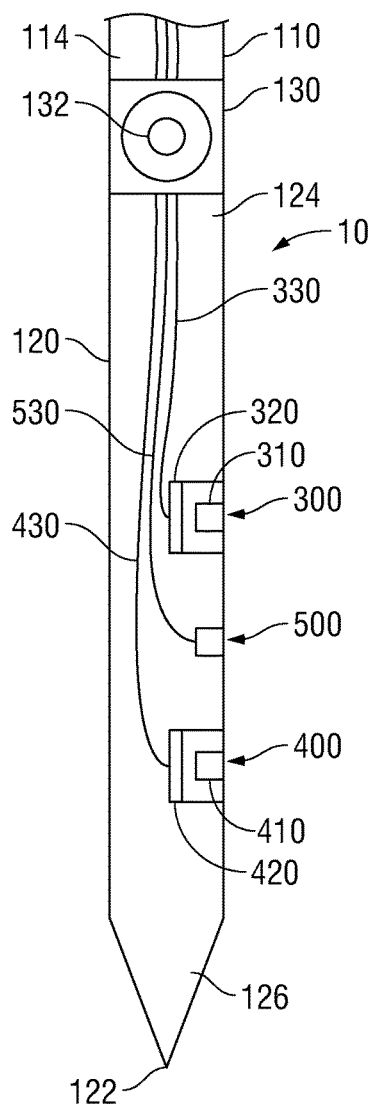
FIG. 3 is an enlarged, cross-sectional view of the distal portion of the surgical camera assembly of FIG. 1.

Turning now to FIG. 3, and as mentioned above, surgical cameras 300, 400 are each positioned to receive an image of the generally conically-shaped area "A1" and "A2" (FIG. 1), respectively, extending outwardly from the outer periphery of distal member 120, while illumination source 500 is disposed therebetween for illuminating the surgical site "S" (FIGS. 4-6) for better visualization thereof. More specifically, each camera assembly 300, 400 includes a lens 310, 410 configured to receive the images of areas "A1" and "A2," respectively. Surgical cameras 300, 400 each further include an image sensor 320, 420 positioned within distal member 120 and configured to receive the optical image projected thereon by lenses 310, 410, respectively. Image sensors 320, 420, in turn, convert the optical image received from lenses 310, 410, respectively, into an electrical signal. Image sensors 320, 420 may be CCD image sensors, CMOS image sensors, or any other suitable image sensors as is known in the art.

With continued reference to FIG. 3, image sensors 320, 420 are electrically coupled to an insulated wire, or bundle of wires 330, 430, respectively, that extends from image sensors 320, 420 proximally though distal member 120, pivot assembly 130 and proximal member 110 of surgical camera assembly 10. Each wire(s) 330, 430 transmits the electrical signal produced by image sensors 320, 420, respectively, through surgical camera assembly 10 to control circuitry (not explicitly shown) disposed within proximal member 110, support platform 200, or an external control unit (not shown). A wire 530 coupled to illumination source 500 may similarly extend proximally through surgical camera assembly 10. Wires 330, 430, 530 may also be configured to transfer power to image sensors 320, 420 and illumination source 500, respectively, from a battery (not shown) disposed within surgical camera assembly 10 or from an external power source (not explicitly shown).

Figure 7:
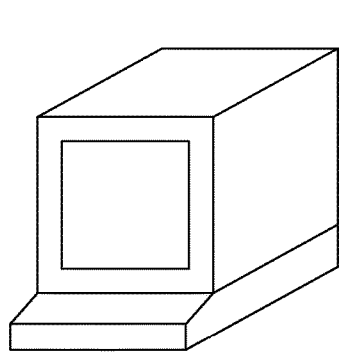
FIG. 7 is a perspective view of a video monitor for use in conjunction with the surgical camera assembly of FIG. 1.
Figure 8:
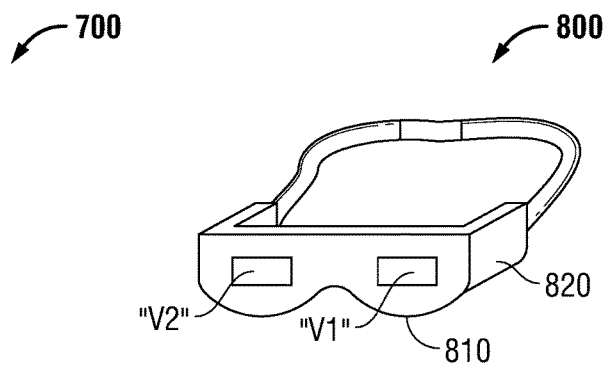
FIG. 8 is a perspective view of a pair of visualization goggles for use in conjunction with the surgical camera assembly of FIG. 1.

Referring now to FIGS. 7-8, in conjunction with FIG. 3, the control circuitry (not shown) processes, modulates, and/or synthesizes the signals from image sensors 320, 420, respectively, and outputs a video signal for display on a video monitor 700 (FIG. 7), visualization goggles 800 (FIG. 8), or other suitable display. More specifically, the signals corresponding to the offset images of areas "A1" and "A2" (FIG. 1) are multiplexed or synthesized to produce an electronically synthesized three-dimensional video image for display on the video monitor 700. Surgical camera assembly 10 is configured to produce a sharp, reliable three-dimensional video image of the internal surgical site "S" (FIGS. 4-6) as a result of the fixed positioning of surgical cameras 300, 400 relative to one another, thus inhibiting distortion of the image or other imaging problems that may result from relative movement between the cameras 300, 400. When used in conjunction with visualization goggles 800, the signals corresponding to the offset images of areas "A1" and "A2" (FIG. 1) are displayed on lens 810 of visualization goggles 800 as video images "V1" and "V2," respectively. Accordingly, with the two-dimensional video images "V1" and "V2" of areas "A1" and "A2" (FIG. 1), respectively, displayed to the surgeon directly in front of each of the surgeons eyes, a three-dimensional image is seen by the surgeon. Control electronics (not explicitly shown) within headset 820 of goggles 800 may be used to reposition the images "V1" and "V2" on lens 810 as desired for optimal viewing by the surgeon and/or to make the images "V1" and "V2" transparent so as to permit the surgeon to maintain visualization of the surgeon's surroundings through lens 810 in addition to viewing the images "V1" and "V2." The images "V1" and "V2" are likewise sharp, reliable video images of the internal surgical site "S" (FIGS. 4-6).

Turning now to FIGS. 4-6, the use and operation of surgical camera assembly 10 is described. Initially, surgical camera assembly 10 is coupled to support platform 200 (FIG. 1), if desired, and distal member 120 is disposed in the initial position, wherein distal member 120 is substantially aligned with proximal member 110 and longitudinal axis "X-X" of surgical camera assembly 10. In this position, as shown in FIG. 4, surgical camera assembly 10 may be advanced relative to tissue "T" such that distal tip 122 of distal member 120 contacts tissue "T" and, ultimately, penetrates, or punctures tissue "T" to allow surgical camera assembly 10 to be inserted through the puncture, or incision "I" in tissue "T" and into the internal surgical site "S." As mentioned above, arm 210 of support platform 200 (see FIG. 1) may be manually or robotically controlled for advancing surgical camera assembly 10 relative to tissue "T" to puncture tissue "T" with distal tip 122 of surgical camera assembly 10 and to insert surgical camera assembly 10 further into (or retract surgical camera assembly 10 from) the internal surgical site "S."

As shown in FIG. 5, surgical camera assembly 10 is inserted a sufficient depth into the surgical site "S" such that distal member 120 and pivot assembly 130 are completely disposed within the internal surgical site "S" and such that at least a portion of proximal member 110 is disposed within the internal surgical site. This positioning, as can be appreciated, allows distal member 120 to be pivoted about pivot pin 132 of pivot assembly 130 and relative to proximal member 110 without substantially affecting tissue "T."

Once this position has been achieved, surgical camera assembly 10 may be rotated about longitudinal axis "X-X" and/or distal member 120 may be pivoted from the initial, substantially aligned position, to the second, angled position relative to longitudinal axis "X-X" to orient lenses 310, 410 of surgical cameras 300, 400, respectively, in a desired viewing direction "D," as shown in FIG. 6. Thereafter, surgical cameras 300, 400 and illumination source 500 may be activated such that, as mentioned above, a three-dimensional video image of the internal surgical site "S," as seen in viewing direction "V," is transmitted to an external video display, e.g., video monitor 700 (FIG. 7), visualization goggles 800 (FIG. 8), or other suitable display, for viewing by the surgeon. Arm 210 of support platform 200 (FIG. 1) may further be manipulated to advance or retract surgical camera assembly 10, surgical camera assembly 10 may be rotated about longitudinal axis "X-X," and/or distal member 120 may be angled further off or back towards longitudinal axis "X-X" to reposition cameras 300, 400 in a desired viewing direction "D" to view a desired area of the internal surgical site "S."

When viewing is complete, i.e., at the end of the surgical procedure to be performed, distal member 120 of surgical camera assembly 10 is returned to the initial, aligned position and surgical camera assembly 10 is withdrawn from the incision "I" in tissue "T." Surgical camera assembly 10 may be configured to have a relatively small diameter such that a relatively small incision "I" in formed within tissue "T," thus reducing trauma and discomfort to the patient as well as reducing healing time required to heal the incision "I" in tissue "T."

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical camera assembly, comprising:
an elongated proximal member defining a longitudinal axis;
an elongated distal member defining a pointed distal tip configured to puncture tissue to permit insertion of the surgical camera assembly at least partially into an internal surgical site, the elongated distal member pivotably coupled to the elongated proximal member and movable relative thereto between a first position, wherein the elongated distal member is substantially aligned with the elongated proximal member and the longitudinal axis, and a second position, wherein the elongated distal member is angled off of the longitudinal axis; and
first and second surgical cameras fixedly disposed within the elongated distal member, each of the first and second surgical cameras oriented to define a viewing area in a direction extending from an outer lateral periphery of the elongated distal member, the first and second surgical cameras fixed in position relative to one another and longitudinally spaced-apart from one another, the first and second surgical cameras configured to produce first and second video images, respectively, that are used in conjunction with one another to provide a three-dimensional video image of the internal surgical site.

2. The surgical camera assembly according to claim 1, further comprising an illumination source disposed between the first and second surgical cameras, the illumination source configured to illuminate the internal surgical site to facilitate imaging thereof.

3. The surgical camera assembly according to claim 1, further comprising a support platform including a base and a support arm, the support arm configured to releasably support the surgical camera assembly at a free end thereof.

4. The surgical camera assembly according to claim 3, wherein the support arm is operable to manipulate the surgical camera assembly for insertion of the surgical camera into and positioning of the surgical camera within the internal surgical site.

5. The surgical camera assembly according to claim 4, wherein the support arm is manually controlled.

6. The surgical camera assembly according to claim 4, wherein the support arm is robotically controlled.

\* \* \* \* \*